(12) United States Patent
Cloyd et al.

(10) Patent No.: US 9,770,407 B2
(45) Date of Patent: *Sep. 26, 2017

(54) PARENTERAL CARBAMAZEPINE FORMULATION

(71) Applicant: Lundbeck Pharmaceuticals LLC, Deerfield, IL (US)

(72) Inventors: James Cloyd, Edina, MN (US); Angela Birnbaum, Minneapolis, MN (US); Ilo Leppik, Minneapolis, MN (US); Stephen D. Collins, Lake Forest, IL (US)

(73) Assignee: LUNDBECK PHARMACEUTICALS LLC, Deerfield, IL (US)

(*) Notice: Subject to any disclaimer, the term of this patent is extended or adjusted under 35 U.S.C. 154(b) by 780 days.

This patent is subject to a terminal disclaimer.

(21) Appl. No.: 14/051,938

(22) Filed: Oct. 11, 2013

(65) Prior Publication Data

US 2014/0080812 A1 Mar. 20, 2014

Related U.S. Application Data

(63) Continuation of application No. 12/571,039, filed on Sep. 30, 2009, which is a continuation of application No. 11/542,520, filed on Oct. 2, 2006, now abandoned.

(60) Provisional application No. 60/722,692, filed on Sep. 30, 2005.

(51) Int. Cl.
| | | |
|---|---|---|
| *A01N 43/04* | (2006.01) |
| *A61K 31/715* | (2006.01) |
| *A01N 43/46* | (2006.01) |
| *A01N 43/00* | (2006.01) |
| *A61K 31/55* | (2006.01) |
| *A61K 9/00* | (2006.01) |
| *A61K 31/724* | (2006.01) |
| *C08B 37/16* | (2006.01) |
| *A61K 47/40* | (2006.01) |

(52) U.S. Cl.
CPC ............ *A61K 9/0019* (2013.01); *A61K 31/55* (2013.01); *A61K 31/724* (2013.01); *A61K 47/40* (2013.01); *C08B 37/0012* (2013.01); *C08B 37/0015* (2013.01)

(58) Field of Classification Search
CPC ...... A61K 9/009; A61K 31/55; A61K 31/724; A61K 47/40; C08B 37/0012; C08B 37/0015
USPC .................................................. 514/58, 217
See application file for complete search history.

(56) References Cited

U.S. PATENT DOCUMENTS

| | | |
|---|---|---|
| 3,459,731 A | 8/1969 | Gramera et al. |
| 5,134,127 A | 7/1992 | Stella et al. |
| 5,231,089 A | 7/1993 | Bodor |
| 5,376,645 A | 12/1994 | Stella et al. |
| 5,646,131 A | 7/1997 | Badwan et al. |
| 6,046,177 A | 4/2000 | Stella et al. |
| 6,153,746 A | 11/2000 | Shah et al. |
| 6,218,375 B1 | 4/2001 | Raghavan et al. |
| 6,232,304 B1 | 5/2001 | Kim et al. |
| 6,458,770 B1 | 10/2002 | Van Hoogevest |
| 6,546,131 B1 | 4/2003 | Mizoguchi et al. |
| 6,632,803 B1 | 10/2003 | Harding |
| 6,858,584 B2 | 2/2005 | Judice et al. |
| 6,869,939 B2 | 3/2005 | Mosher et al. |
| 7,115,587 B2 | 10/2006 | Nerurkar et al. |
| 7,544,364 B2 | 6/2009 | Judice et al. |
| 7,629,331 B2 | 12/2009 | Pipkin et al. |
| 7,635,773 B2 | 12/2009 | Antle |
| 8,158,580 B2 | 4/2012 | Judice et al. |
| 2003/0055023 A1 | 3/2003 | Rajewski et al. |
| 2004/0157796 A1 | 8/2004 | Gokarn |
| 2007/0020298 A1 | 1/2007 | Pipkin et al. |

FOREIGN PATENT DOCUMENTS

| | | |
|---|---|---|
| AU | 1320095 A | 7/1995 |
| CA | 2463687 A1 | 4/2003 |
| EP | 1928464 A2 | 6/2008 |
| JP | 9-506889 | 7/1997 |

(Continued)

OTHER PUBLICATIONS

Ansel, H.C. et al. (1999) Chapter 4. "Dosage Form Design: Biopharmaceutic and Pharmacokinetic Considerations" in Pharmaceutical Dosage Forms and Drug Delivery Systems, 7$^{th}$ Edition. Published by Lippincott Williams & Wilkins, pp. 101-141.*
El-Gindy, G.A., Mohammed, F.A., Salem, S.Y. (2002) Preparation, pharmacokinetic and pharmacodynamic evaluation of carbamazepine inclusion complexes with cyclodextrins. S.T.P. Pharma Sciences, vol. 12, No. 6, p. 369-378.
Becirevic-Lacan M., Jug, M., Bacic-Vrca, V., Cetina-Cizmek, B. (2002) Development of o/w emulsion formulation for carbamazepine by using modified cyclodextrins. Acta Pharm., v. 52, p. 149-159.

(Continued)

*Primary Examiner* — Scarlett Goon
(74) *Attorney, Agent, or Firm* — Wilmer Cutler Pickering Hale and Dorr LLP

(57) ABSTRACT

The present invention is directed to a carbamazepine-cyclodextrin inclusion complex useful for the parenteral administration of carbamazepine. The carbamazepine-cyclodextrin inclusion complex is prepared by the admixture of a modified cyclodextrin and carbamazepine in a physiologically acceptable fluid. Modified cyclodextrins include 2-hydroxypropyl-beta-cyclodextrin and sulfoalkyl cyclodextrins. More particularly, the sulfoalkyl cyclodextrins are those described and disclosed in U.S. Pat. Nos. 5,134,127 and 5,376,645. A physiologically acceptable fluid includes sterile isotonic water, Ringer's lactate, D5W (5% dextrose in water), physiological saline, and similar fluids suitable for parenteral administration.

30 Claims, 6 Drawing Sheets

(56) References Cited

FOREIGN PATENT DOCUMENTS

| | | |
|---|---|---|
| JP | 2002-534472 | 10/2002 |
| WO | WO-91/11172 | 8/1991 |
| WO | WO-93/10794 | 6/1993 |
| WO | WO-95/17191 | 6/1995 |
| WO | WO-97/41896 | 11/1997 |
| WO | WO-98/58677 | 12/1998 |
| WO | WO-03/043602 | 5/2003 |

OTHER PUBLICATIONS

Betlach, C.J., Gonzalez, M.A., McKiernan, B.C., Neff-Davis, C., Bodor, N. (1993) Oral Pharmacokinetics of Carbamazepine in Dogs from Commercial Tablets and a Cyclodextrin Complex. Journal of Pharmaceutical Sciences, vol. 82, No. 10, pp. 1058-1060.
Final Office Action dated Oct. 31, 2013 in co-pending U.S. Appl. No. 13/547,866, 36 pgs.
Aldenkamp, A. P., et al., "Controlled Release Carbamazepine: Cognitive Side Effects in Patients with Epilepsy", Epilepsia, 1987, vol. 28, No. 5, pp. 507-514.
Ansel, Howard. C., et al., Pharmaceutical Dosage Forms and Drug Delivery Systems, 7th Edition, Chapter 2, Published by Lippincott Williams & Wilkins, 1999, pp. 23-59.
Brewster et al., "Development of aqueous parenteral formulations for carbamazepine through the use of modified cyclodextrins," J. Pharm. Sci., vol. 80, No. 4, Apr. 1991,380-383.
Brewster, M.E. et al., "Intravenous and oral pharmacokinetic evaluation of a 2-hydroxypropyl-β-cyclodextrin-based formulation of carbamazepine in the dog: Comparison with commercially available tablets and suspensions," Journal of Pharmaceutical Sciences, vol. 86(3); pp. 335-339 (1997).
Brewster, Marcus E., et al., "Solubilization of itraconazole as a function of cyclodextrin structural space", J. Incl. Phenom Macrocycl. Chem., 2007, vol. 57, pp. 561-566.
Campbell, F. G. et al., "Clinical trial of carbamazepine (Tegretol) in trigeminal neuralgia", J. Neurol. Neurosurg. Psychiat., 1966, vol. 29, pp. 265-267.
Challa, Rajeswari, et al., "Cyclodextrins in Drug Delivery: An Updated Review", AAPS PharmSciTech, 2005, vol. 6, No. 2, Article 43, pp. E329-E357.
Cloyd, J.C. et al., "Factors affecting antiepileptic drug pharmacokinetics in community-dwelling elderly," Int. Rev. Neurobiol, vol. 81, pp. 201-210 (2007).
Final Office Action dated Jul. 2, 2013 in co-pending U.S. Appl. No. 13/679,715, 29 pages.
U.S. Office Action issued from related U.S. Appl. No. 13/679,715, dated Mar. 7, 2013, 24 pages.
Cui Shanfeng, "Dissolution Test of Beta-cyclodextrin-Carbamazepine Dispersible Tablet" Northwest Pharmaceuticals, Aug. 2000, 4, p. 167, (English translation 3 pages).
Edwards A.D. et, "Time-resolved x-ray scattering using synchrotron radiation applied to the study of a polymorphic transition in carbamazepine," J. Pharm. Sci, vol. 90(8), pp. 1106-1114 (Aug. 2001).
English Translation of Japanese Office action issued on Apr. 18, 2012 for Japanese Application No. 2008-533754 (4 pages).
Food and drug administration, "Route of administration," In: Center for Drug Evaluation and research's Data Standards manual (monographs), pp. 1-4.
Food and Drug Administration,"Statistical approaches to establishing Bioequivalence in center for drug Evaluation and research's Guidance for industry,". U.S. Department of Health and Human Services, pp. 1-48 (2001).
Gerardin et al., "Absolute bioavailability of carbamazepine after oral administration of a 2% syrup," Epilepsia 1990; 31 (3):334-338.
Graves, Nina M., et al., "Relative Bioavailability of Rectally Administered Carbamazepine Suspension in Humans", Epilepsia, 1985, vol. 26, No. 5, pp. 429-433.

Haleblian, John, et al., "Pharmaceutical Applications of Polymorphism, Journal of Pharmaceutical Sciences", Aug. 1969, vol. 58, No. 8, pp. 911-929.
Hoppener, R. J., et al., "Correlation Between Daily Fluctuations of Carbamazepine Serum Levels and Intermittent Side Effects", Epilepsia, 1980, vol. 21, pp. 341-350.
International Preliminary Report on Patentability (IPRP) for International Application No. PCT/US2006/038508, dated Apr. 1, 2008.
International Search Report and Written opinion for International Application PCT/US06/38508, dated Jul. 11, 2007.
Killian, James M., et al., "Carbamazepine in the Treatment of Neuralgia", Arch. Neurol., Aug. 1968, vol. 19, pp. 129-136.
Knake et al., "Status epilepticus: A critical review", Epilepsy & Behavior, vol. 15, pp. 10-14 (2009).
Koster, Andries, et al., "Presystemic and Systemic Intestinal Metabolism of Fenoterol in the Conscious Rat", Drug Metabolism and Disposition, 1985, vol. 13, No. 4, pp. 464-470.
Lin J.H. ,"Species similarities and differences in pharmacokinetics," Drug Metabolism and Disposition, 23, vol. 10: 1008-1021 (1995).
Loftsson, Thorsteinn, et al., "Cyclodextrins in drug delivery", Expert Opin. Drug Deliv., 2005, vol. 2, No. 2, pp. 335-351.
Loftsson, Thorsteinn, et al., "Evaluation of cyclodextrin solubilization of drugs", International Journal of Pharmaceutics, 2005, vol. 302, pp. 18-28.
Loftsson, Thorsteinn, et al., "Pharmaceutical Applications of Cyclodextrins. 1. Drug Solubilization and Stabilization", Journal of Pharmaceutical Sciences, Oct. 1996, vol. 85, No. 10, pp. 1017-1025.
MacPhee, Graeme J. A., et al., "Intradose and Circadian Variation in Circulating Carbamazepine and Its Epoxide in Epileptic Patients: A Consequence of Autoinduction of Metabolism", Epilepsia, 1987, vol. 28, No. 3, pp. 286-294.
Mistry, M., et al., "Quantitation of Extrahepatic Metabolism: Pulmonary and Intestinal Conjugation of Naphthol", Drug Metabolism and Disposition, 1985, vol. 13, No. 6, pp. 740-745.
Mizuma, Takashi, "Kinetic Impact of Presystemic Intestinal Metabolism on Drug Absorption: Experiment and Data Analysis for the Prediction of In Vivo Absorption from In Vitro Data", Drug Metab. Pharmacokin., 2002, vol. 17, No. 6, pp. 496-506.
Morselli, Paolo L., "Carbamazepine Absorption, Distribution and Excretion", Antiepileptic Drugs, Third Edition, edited by Levy, R. et al., 1989, Raven Press, Ltd., New York, Chapter 3, pp. 473-490.
Mosher, et al., "Complexation and Cyclodextrins," Encyclopedia of Pharmaceutical Technology. Marcel Dekker, Inc.; New York, 2002, 531-558.
Müller, Adolf A., et al., "Carbamazepine and Oxcarbazepine in the Treatment of Manic Syndromes—Studies in Germany", Anticonvulsants in Affective Disorders, edited by Emrich, H. M., et al., Excerpta Medica, 1984, pp. 139-147.
Osterloh et al., "The absence of isotopic effect during the elimination of deuterium labeled carbamazepine in the rat," Life Science, vol. 23, pp. 83-87 (1978).
Perucca et al., Pharmacological and clinical aspects of antiepileptic drug use in the elderly, Epilepsy Res., vol. 68 suppl. 1, pp. S49-S63 (Jan. 2006).
Porter, Roger J., et al., "Efficacy and Choice of Antiepileptic Drugs", Advances in Epileptology, edited by Meinardi, H., et al., 1977, Amsterdam, Proceedings of the 13th Congress of the International League Against Epilepsy, and 9th Symposium of the International Bureau for Epilepsy, pp. 220-231.
Post, Robert M., et al., "Efficacy of Carbamazepine in Affective Disorders: Implications for Underylying Physiological and Biochemical Substrates", Anticonvulsants in Affective Disorders, edited by Emrich, H. M., et al., Excerpta Medica, 1984, pp. 93-115.
Remmel et al., "Dose-dependent pharmacokinetics of carbamazepine in rats: determination of the formation clearance of carbamazepine-10, 11-epoxide," Pharm. Res, vol. 7, pp. 513-517 (May 1990).
Riva, Roberto, et al., "Diurnal Fluctuations in Free and Total Steady-State Plasma Levels of Carbamazepine and Correlation with Intermittent Side Effects", Epilepsia, 1984, vol. 25, No. 4, pp. 476-481.

(56) References Cited

OTHER PUBLICATIONS

Rowe et al., "Cyclodextrins" in Handbook of Pharmaceutical Excipients, published by the Pharmaceutical Press, pp. 217-221 (2006).
Savolainen, Jouko, et al., "Co-Administration of a Water-Soluble Polymer Increases the Usefulness of Cyclodextrins in Solid Oral Dosage Forms", Pharmaceutical Research, 1998, vol. 15, No. 11, pp. 1696-1701.
Sinz et al. ,"Analysis of lamotrigine and lamotrigine 2-N-glucuronide in guinea pig blood and urine by reserved-phase ion-pairing liquid chromatography," J. Chromatogr., vol. 571, pp. 217-230 (1991).
Smith et al., "Effect of SBE7-beta-cyclodextrin complexation on carbamazepine release from sustained release beads," Euro. Journal of Pharmaceutics and Biopharmaceutics, vol. 60, pp. 73-80 (May 2005).
Spina E., Carbamazepine. Chemistry, biotransformation, and pharmacokinetics, 2002, Ch. 21 In: Levy R.H., et al. (eds.), antiepileptic Drugs, 5th ed., Philadelphia, PA, Lippincott, Williams & Wilkins, 236-246.
Stella et al., "Mechanisms of drug release from cyclodextrin complexes," Adv. Drug. Deliv., vol. 36, pp. 3-16 (Mar. 1999).
Supplementary European Search Report (SESR), completed Sep. 1, 2009, mailed Sep. 9, 2009.
Szejtli J., "Ciclodextrins in Drug Formulations: Part II," Pharmaceutical Technology, pp. 24-38 (Aug. 1991).
Taylor, J. C., et al., "Long-term treatment of trigeminal neuralgia with carbamazepine", Postgraduate Medical Journal, Jan. 1981, vol. 57, pp. 16-18.
Thompson D.O., Cyclodextrins-enabling excipients: their present and future use in pharmaceuticals, Crit. Rev. Ther. Drug. Carrier Syst., Vil 14(1), pp. 1-104 (1997).
Thompson, Diane, et al., "Cyclodextrins (CDS)—Excipients by Definition, Drug Delivery Systems by Function (Part I: Injectable Applications)", Drug Delivery Technology, 2002, vol. 2, No. 7, pp. 34, 36 and 38.
Tomson, Torbjörn, "Interdosage Fluctuations in Plasma Carbamazepine Concentration Determine Intermittent Side Effects", Arch. Neurol., Aug. 1984, vol. 41, pp. 830-834.
Ueda et al., "Evaluation of a Sulfobutyl Ether β-Cyclodextrin as a Solubilizing/Stabilizing Agent for several drugs," Drug Development and Industrial Pharmacy, vol. 24(9), pp. 863-867 (1998).
Uekama et al., "Stabilizing and Solubilizing effects of Sulfobutyl Ether β-Cyclodextrin on prostaglandin $E_1$ Analogue," Pharm. Res., vol. 18, pp. 1578-85 (Nov. 2001).
Uekama, Kaneto, "Design and Evaluation of Cyclodextrin-Based Drug Formulation", Chem. Pharm. Bull., 2004, vol. 52, No. 8, pp. 900-915.
Wilkinson G.R., "Pharmacokinetics: the Dynamics of Drug absorption, distribution, and elimination," Goodman and Gilman's the Pharmacological Basis of Therapeutics, Hardman, J.G. and Limbird, L.E. (eds.), the McGraw Hill Companies, Inc. pp. 3-26 (2001).
Non-Final Office Action dated Mar. 7, 2013 in co-pending U.S. Appl. No. 13/679,715, 16 pages.
Non-Final Office Action dated Mar. 25, 2013 in co-pending U.S. Appl. No. 13/547,866, 16 pages.
Sillanpää M. Carbamazepine. Pharmacology and clinical uses. Acta Neurol Scand Suppl. 1981;88, 187 pages.
Ueda H, Ou D, Endo T, Nagase H, Tomono K, Nagai T. Evaluation of a sulfobutyl ether beta-cyclodextrin as a solubilizing/stabilizing agent for several drugs. Drug Dev Ind Pharm. Sep. 1998;24(9):863-7.
Löscher W, Hönack D. Intravenous carbamazepine: comparison of different parenteral formulations in a mouse model of convulsive status epilepticus. Epilepsia. Jan. 1997;38(1):106-13.
Löscher W, Hönack D, Richter A, Schulz HU, Schürer M, Düsing R, Brewster ME. New injectable aqueous carbamazepine solution through complexing with 2-hydroxypropyl-beta-cyclodextrin: tolerability and pharmacokinetics after intravenous injection in comparison to a glycofurol-based formulation. Epilepsia. Mar. 1995;36(3):255-61.
Rajewski RA, Traiger G, Bresnahan J, Jaberaboansari P, Stella VJ, Thompson DO. Preliminary safety evaluation of parenterally administered sulfoalkyl ether beta-cyclodextrin derivatives. J Pharm Sci. Aug. 1995;84(8):927-32.
MIMS, "British National Formulary" UK: Pharmaceutical Press, 2005, 3 pages.
Cyclodextrins General, filed with then-applicant's letter of Nov. 4, 2011, 5 pages.
Excipients Technology by ISP, filed with then-applicant's letter of Nov. 4, 2011, 5 pages.
Communication of a Notice of Opposition mailed on Feb. 16, 2015 for EP Application No. 06816054.8; 67 pages.
Decision Revoking European Patent No. 1 928 464 issued Sep. 26, 2016 by the European Patent Office (10 pages).
Decision of Appeal for U.S. Appl. No. 13/547,866 dated Dec. 19, 2016, 19 pages.
Notice of Allowance for U.S. Appl. No. 13/547,866, dated Mar. 3, 2017, consisting of 26 pages total.

\* cited by examiner

The Whiskers Represent the 10 and 90 Percentile of Cmax

PARENTERAL CARBAMAZEPINE FORMULATION

RELATED APPLICATIONS

This application is a continuation of U.S. patent application Ser. No. 12/571,039, filed Sep. 30, 2009, which is a continuation of U.S. patent application Ser. No. 11/542,520, filed Oct. 2, 2006, which was filed concurrently with International Application No. PCT/US2006/038508, filed Oct. 2, 2006, and which claims priority from U.S. Provisional Patent Application No. 60/722,692, filed Sep. 30, 2005. Each of the aforementioned applications is hereby incorporated herein by reference in its entirety.

BACKGROUND OF THE INVENTION

Carbamazepine, or 5H-dibenz[b,f]azepine-5-carboxamide, is a widely used antiepileptic agent. It is available in the U.S. as Tegretol brand chewable tablets of 100 mg, tablets of 200 mg and suspension of 100 mg/5 mL, intended for oral administration as a treatment for epilepsy or as a specific analgesic for trigeminal neuralgia. Other brand names include Equetro, Carbatrol, Tegretol XR and Epitol. Generic versions of these oral dosage forms are also available. Dosage forms include Carbatrol available in 100, 200, and 300 mg strengths; and Tegretol XR, available in 100, 200, and 400 mg strengths.

As shown in Table 1, recommended maintenance dosage levels in adults and children over 12 years of age are 800-1200 mg daily, although up to 2400 mg daily have been used in adults. In children of 6 to 12 years of age, the maintenance dosage level is usually 20-30 mg/kg/d and in children less than 6 years old the maintenance dosage level is usually 10-20 mg/kg/d.

TABLE 1

Labeled dosage for carbamazepine oral dosage forms.

| Age | Recommended Daily Maintenance Dose | Dosing Frequency (for IR formulations) |
|---|---|---|
| <6 yrs | 10-20 mg/kg | 2-4 doses/day |
| 6-12 yrs | 20-30 mg/kg max dose 1000 mg | 2-4 doses/day |
| Children >12 yrs | 400-1200 mg 1600-2400 mg | 2-4 doses/day |
| Adults-epilepsy | 800-1200 mg some pts require 1600-2400 mg | 3-4 divided doses |
| Adults-trigeminal neuralgia | 400-800 mg max dose 1200 mg | 2 doses/day |
| Adults-bipolar disorder | Doses greater than 1600 mg have not been studied | 2 doses/day |

Note:
only Equetro, an extended release formulation is approved for bipolar disorder.

For complex partial seizures (temporal lobe, psychomotor), carbamazepine is a widely used anticonvulsant drug. It is also of proven efficacy in the treatment of generalized tonic-clonic (grand mal) seizures. Carbamazepine has also been used in treating simple partial (focal or Jacksonian) seizures and in patients with mixed seizure patterns which include the above, or other partial or generalized seizures. It is not used in the treatment of absence seizures (petit mal).

In addition to its proven effectiveness, carbamazepine has, in many respects, a more favorable profile in terms of the incidence and severity of side-effects than other anticonvulsants. Thus, carbamazepine is less sedating and causes less intellectual function impairment than other antiepileptic drugs such as phenobarbital, primidone and phenyloin. Furthermore, carbamazepine does not precipitate gingival hypertrophy, hirsutism, acne or other undesired effects associated with phenyloin. These attributes have helped to make carbamazepine the drug of choice in women and children.

Use of carbamazepine is complicated by incomplete, slow and variable absorption; extensive protein binding; and induction of its own metabolism. From Spina E Chapter 21 in Antiepileptic Drugs 5th edition. Lippincott, Williams & Wilkins, Philadelphia, 2002 pp 236-246 and references cited therein. The absolute bioavailability (the percentage of a dose that reaches the bloodstream) for the immediate release and extended release tablets has previously been estimated to range from 75-85 although the absence of an intravenous formulation has precluded systematic study of the extent and inter-patient variability in absorption.

U.S. Pat. No. 5,231,089 to Bodor mentions the lack of an injectable formulation for carbamazepine, noting that therefore there has not been precise information relating to the drug's absolute bioavailability. In addition, the lack of an injectable formulation for carbamazepine means that there is no method for providing emergent carbamazepine therapy to a patient in need thereof, as occurs when patients are undergoing surgery, have certain gastro-intestinal diseases, are unconscious or have seizures that preclude oral drug administration, or that require rapid re-establishment of steady state plasma levels.

The absence of an intravenous formulation places patients treated with carbamazepine (sometimes referred to herein as CBZ) at substantial medical risk. Sudden discontinuation of CBZ therapy for whatever reason, can expose an individual to potentially life threatening seizure emergencies. The only alternative is to give the patient a different drug that is available as an intravenous formulation. Exposure to a new medications exposes the patient to adverse reactions and unknown efficacy.

Cyclodextrins, sometimes referred to as Schardinger's dextrins, were first isolated by Villiers in 1891 as a digest of *Bacillus amylobacter* on potato starch. The foundations of cyclodextrin chemistry were laid down by Schardinger in the period 1903-1911. Until 1970, however, only small amounts of cyclodextrins could be produced in the laboratory and the high production cost prevented the usage of cyclodextrins in industry. In recent years, dramatic improvements in cyclodextrin production and purification have been achieved and cyclodextrins have become much less expensive, thereby making the industrial application of cyclodextrins possible.

Cyclodextrins are cyclic oligosaccharides with hydroxyl groups on the outer surface and a void cavity in the center. Their outer surface is hydrophilic, and therefore they are usually soluble in water, but the cavity has a lipophilic character. The most common cyclodextrins are α-cyclodextrin, β-cyclodextrin and γ-cyclodextrin, consisting of 6, 7 and 8 α-1,4-linked glucose units, respectively. The number of these units determines the size of the cavity.

Cyclodextrins are capable of forming inclusion complexes with a wide variety of hydrophobic molecules by taking up a whole molecule (a "guest molecule"), or some part of it, into the void cavity. The stability of the resulting complex depends on how well the guest molecule fits into the cyclodextrin cavity. Common cyclodextrin derivatives are formed by alkylation (e.g., methyl-and-ethyl β-cyclodextrin) or hydroxyalkylation of the hydroxyethyl-derivatives of α-, β-, and γ-cyclodextrin) or by substituting the primary hydroxyl groups with saccharides (e.g., glucosyl- and maltosyl-β-cyclodextrin). Hydroxypropyl-β-cyclodextrin and its preparation by propylene oxide addition to β-cyclodextrin, and hydroxyethyl-β-cyclodextrin and its preparation by ethylene oxide addition to β-cyclodextrin, were described in a patent of Gramera et al. (U.S. Pat. No. 3,459,731, issued August 1969) over 35 years ago.

Although cyclodextrins have been used to increase the solubility, dissolution rate and/or stability of a great many compounds, it is also known there are many drugs for which cyclodextrin complexation either is not possible or yields no advantages. See J. Szejtli, Cyclodextrins in Drug Formulations: Part II, Pharmaceutical Technology, 24-38, August, 1991. Despite this potential pharmaceutical utility, certain cyclodextrins are have limitations.

Cyclodextrins and their derivatives are mostly crystalline solids. Concentration of some cyclodextrins in the renal tissue is followed by crystal formation causing necrotic damage to the cells. Despite forming water soluble clathrate complexes, the crystalline cyclodextrin drug complexes have generally been limited in their utility to sublingual or topical administration.

U.S. Pat. Nos. 5,134,127 and 5,376,645, whose disclosures are incorporated herein by reference, are directed to novel cyclodextrin derivatives, in particular sulfoalkyl cyclodextrin derivatives, that overcome the limitations of other cyclodextrins. In particular, the sulfoalkyl cyclodextrin derivatives disclosed therein exhibit lower nephrotoxicity while exhibiting high aqueous solubility.

The present invention is based, inter alia, on the determination that carbamazepine stable inclusion complexes with cyclodextrins are highly water soluble relative to the non-complexed drug. Surprisingly and unexpectedly, the carbamazepine-cyclodextrin inclusion complexes of the invention result in an injectable formulation that provides significant benefits and advantages over other carbamazepine formulations. For example, the carbamazepine-cyclodextrin inclusion complexes of the present invention are completely bioavailable, delivering 100% of the dose to the bloodstream in a consistent and predictable manner which is not the case with solid oral dosage forms. Also, unlike solid oral dosage forms, the carbamazepine-cyclodextrin inclusion complexes of the present invention can be administered to a patient suffering from a generalized tonic-clonic or other acute seizure via a peripheral rather than oral route. The carbamazepine-cyclodextrin inclusion complexes of the present invention satisfy a significant unmet medical need for a stable injectable formulation of carbamazepine that overcomes the limitations of poorly soluble and variably absorbed oral formulations.

SUMMARY OF THE INVENTION

In one aspect, the present invention contemplates a carbamazepine-cyclodextrin inclusion complex useful for the parenteral administration of carbamazepine comprising a carbamazepine complexed with a modified cyclodextrin. Preferably, the modified cyclodextrin is a sulfoalkyl-cyclodextrin. A preferred modified cyclodextrin is sulfobutylether-7-beta-cyclodextrin. The inclusion complex preferably has a concentration of about 5 to about 50 mg/ml carbamazepine, and more preferably a concentration of about 10 mg/ml carbamazepine.

In another aspect, the present invention, there is provided a carbamazepine-cyclodextrin inclusion complex useful for the parenteral administration of carbamazepine in which dosing is about 30% to about 100% of oral maintenance doses, or preferably about 65% to 75% of oral maintenance doses.

In a further aspect, the present invention provides a carbamazepine-cyclodextrin inclusion complex useful for the parenteral administration of carbamazepine having a half-life of about 8 to about 65 hours, and more preferably having a half-life of about 24 hours. In another embodiment, the present invention contemplates a carbamazepine-cyclodextrin inclusion complex useful for the parenteral administration of carbamazepine having an area under the plasma concentration-time curve (AUC) of about 70% to about 130% of the AUC for an oral carbamazepine dosage form, and more preferably having an AUC of about 80% to about 125% of the AUC for an oral carbamazepine dosage form. In a further embodiment, the present invention contemplates a carbamazepine-cyclodextrin inclusion complex useful for the parenteral administration of carbamazepine having a minimum plasma concentration (Cmin) of about 70% to about 130% of the Cmin for an oral carbamazepine dosage form, and more preferably having a Cmin of about 80% to about 125% of the Cmin for an oral carbamazepine dosage form.

In a still further aspect, the present invention provides a carbamazepine-cyclodextrin inclusion complex useful for the parenteral administration of carbamazepine having an intravenous dosing interval of every four to twelve hours, more preferably having an intravenous dosing interval of every six hours, and still more preferably having an intravenous dosing interval of every eight hours.

In another embodiment the present invention provides a method of administering a carbamazepine-cyclodextrin inclusion complex useful for the parenteral administration of carbamazepine comprising: 1) providing a carbamazepine-cyclodextrin inclusion complex; and 2) infusing the complex intravenously to a patient in need thereof every four to twelve hours.

Preferably, the period of infusing occurs over about 5 to about 60 minutes, more preferably over 30 minutes and still more preferably over 5 minutes. Preferably, the infusing is done every six hours, or in another aspect every eight hours.

In a still further embodiment, the present invention provides a method of preparing a carbamazepine-cyclodextrin inclusion complex by admixing a modified cyclodextrin and carbamazepine in a physiologically acceptable fluid to form a carbamazepine-cyclodextrin inclusion complex. In another aspect, the method further includes the step of sterilizing the carbamazepine-cyclodextrin inclusion complex. Preferably, the physiologically acceptable fluid is isotonic. Preferably, the modified cyclodextrin is a sulfoalkyl-cyclodextrin. The modified cyclodextrin is more preferably sulfobutylether-7-beta-cyclodextrin.

BRIEF DESCRIPTION OF THE DRAWINGS

FIG. 1A represents the compiled solubility data.

FIG. 1B represents the averaged solubility data.

DETAILED DESCRIPTION OF THE INVENTION

Figure 1A:
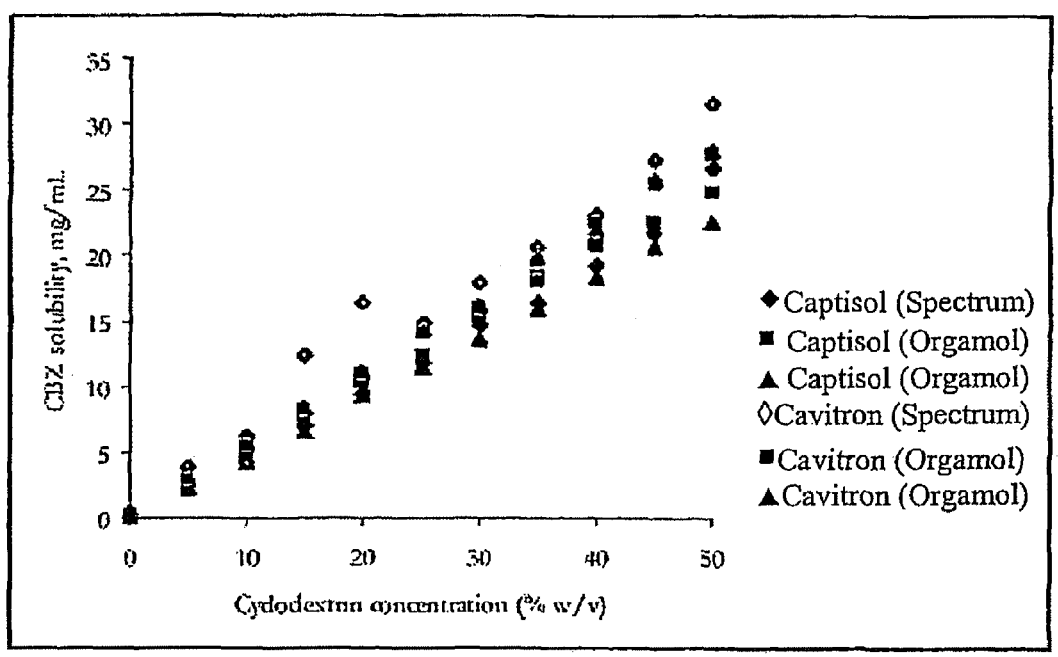
FIGS. 1A-1B show carbamazepine phase solubility as a function of cyclodextrin concentration at ambient laboratory temperature.

The present invention is directed to a carbamazepine-cyclodextrin inclusion complex useful for the parenteral administration of carbamazepine.

As used herein, the term "parenteral" is given its ordinary and customary meaning in the field of pharmaceutical drug routes of administration. According to the Food and Drug Administration's Center for Drug Evaluation and Research Data Standards Manual (CDER Data Element Number C-DRG-00301; Data Element Name: Route of Administration) "parenteral" refers to administration by injection, infusion or implantation. Injection and infusion include administration into a vein (intravenous), into an artery (intraarterial), into a muscle (intramuscular), under the skin (subcutaneous), and into the peritoneum (intraperitoneal). Intrapulmonary (administration within the lungs or its bronchi) and nasal (administration into the nose or by way of the nose) is also contemplated. Any appropriate route of administration set forth in the above-referenced Food and Drug Administration document is specifically included within the scope of the instant invention, and nothing herein shall be construed to limit in any way those routes of administration that would be useful in connection with the carbamazepine-cyclodextrin inclusion complex of the present invention.

In one embodiment, the carbamazepine-cyclodextrin inclusion complex is prepared by the admixture of a modified cyclodextrin and carbamazepine in a physiologically acceptable fluid. Modified cyclodextrins include 2-hydroxypropyl-beta-cyclodextrin and sulfoalkyl cyclodextrins. More particularly, the sulfoalkyl cyclodextrins are those described and disclosed in U.S. Pat. Nos. 5,134,127 and 5,376,645. A physiologically acceptable fluid includes sterile isotonic water, Ringer's lactate, D5W (5% dextrose in water), physiological saline, and similar fluids suitable for parenteral administration.

After an admixture of the modified cyclodextrin and carbamazepine is prepared, the admixture can be sterilized. Sterilization can be by methods well known to those of ordinary skill in the art, such as by autoclaving or by sterile filtration such as passage through a 0.22 micron filter. After-sterilization, the carbamazepine-cyclodextrin inclusion complex can be directly packaged into sterile ampoules, containers for fluids suitable for intravenous administration, or the complex can be lyophilized for prolonged storage according to techniques well known in the art.

The carbamazepine-cyclodextrin inclusion complex can be prepared so that the concentration of carbamazepine ranges from 1 mg/ml to 50 mg/ml, more preferably from 1 mg/ml to 10 mg/ml, and most preferably about 10 mg/ml. Variations in the carbamazepine concentration in the carbamazepine-cyclodextrin inclusion complex of the present invention is conventionally accomplished by varying the amount of carbamazepine used in the preparation of that inclusion complex, as described elsewhere herein.

The carbamazepine-cyclodextrin inclusion complex can be administered parenterally in a single dose of up to 1600 mg, or preferably up to 500 mg, more preferably divided doses from 20 to 500 mg, and most preferably divided doses from 75 to 400 mg. Dosing is dependent upon the indication of the patient being treated, as well as interactions with other drugs that the patient can be taking, and other clinical considerations well within the skill of the attending physician.

The carbamazepine-cyclodextrin inclusion complex of the present invention has a bioavailability of 100% and a half-life of about 24 hours. Resultant plasma concentrations after intravenous administration are reasonably predictable with every 1 mg/kg dose producing an increase in CBZ concentration of 0.75.+−. 0.2 mg/L. Given an average oral bioavailability of 65-75%, the initial IV replacement dose will be 65-75% of a patient's maintenance dose although some adjustment in subsequent IV doses may be necessary depending on a patient's actual oral CBZ bioavailability. This dosing regimen is selected in order to ensure that trough CBZ concentrations remain within the therapeutic range, while minimizing the risk of adverse events associated with elevated, end-of-infusion of CBZ concentrations.

The carbamazepine-cyclodextrin inclusion complex of the present invention preferably has certain pharmacokinetic parameters statistically similar to those of oral CBZ dosage forms. For example, the carbamazepine-cyclodextrin inclusion complex preferably has a minimum plasma concentration (Cmin) of about 70% to about 130% of the Cmin of an oral CBZ dosage form, and more preferably from about 80% to about 125% of the Cmin of an oral CBZ dosage form. Similarly, the carbamazepine-cyclodextrin inclusion complex has an area under the plasma concentration-time curve (AUC) of about 70% to about 130% of the AUC of an oral CBZ dosage form, and more preferably from about 80% to about 125% of the AUC of an oral CBZ dosage form. Workers of ordinary skill in the art of pharmaceutical formulation are well acquainted with these concepts, which are further explained in the Food and Drug Administrations' Guidance for Industry entitled "Statistical Approaches to Establishing Bioequivalence" of January 2001 (see the world wide web fda.gov/cder/guidance/3616fnl.htm.)

The total daily intravenous (IV) dose can be administered as four equal doses every six hours, infused over up to 60 minutes, or preferably over 30 minutes, or more preferably over 15 minutes. As is well known in the art, the infusion duration and dosing interval can be adjusted depending upon clinical considerations within the skill of the attending physician. For example, in a situation where rapid return to steady-state levels of CBZ is desired, the infusion duration can be as short as 2-5 minutes via IV push or IV bolus administration to a patient in need thereof. In other embodiments, the total daily IV dose can be administered as three equal doses every eight hours, infused over up to 60 minutes, or preferably over 30 minutes, or more preferably over 15 minutes. In further embodiments, administration can be continuous, or can be administered using a patient controlled device that permits controlled dosing on an as needed basis. Other dosing schedules are well known in the art, and can be readily determined by pharmacists and physicians skilled in the art based upon considerations of, for example, age of the patient, indication, divided dose and total daily dosage.

In other embodiments, the carbamazepine-cyclodextrin inclusion complexes of the present invention can be administered via rectal, oral or nasal routes for those patients who either cannot tolerate parenteral administration or who are so young that parenteral administration is not practical. In addition, those patients who can receive the formulation of the present invention via an enteral route will obtain the benefits of substantially complete bioavailability over present sold oral dosage forms. Enteral administration does not require a change in the formulation of the present invention, as those carbamazepine-cyclodextrin inclusion complexes can be directly delivered enterally. Taste masking formulations, well known in the art, can be used to modify formulations designed to be administered orally to eliminate any unpleasant taste. Taste masking is, however, related to patient compliance rather than related to efficacy of the present invention for enteral administration.

The carbamazepine-cyclodextrin inclusion complexes of the present invention can be administered to a mammal in need of CBZ treatment. The word "mammal" is given its ordinary and customary meaning in the art, and includes human beings. Accordingly, the carbamazepine-cyclodextrin inclusion complexes of the present invention can be used in veterinary applications as well as the treatment of human conditions. With respect to human treatment, the carbamazepine-cyclodextrin inclusion complexes of the present invention is particularly well suited for pediatric administration, because the instant formulation does not require a peroral route of administration.

The carbamazepine-cyclodextrin inclusion complexes of the present invention can be used for any indication for which CBZ is used. For example, CBZ is indicated for seizure disorders such as partial seizures with complex symptoms (psychomotor, temporal lobe epilepsy), generalized tonic-clonic (grand mal) seizures, mixed seizure patterns or other partial or generalized seizures. CBZ is also indicated for trigeminal neuralgia (tic douloureux) such as treatment of pain associated with true trigeminal neuralgia and bipolar disorders. CBZ is also beneficial in glossopharyngeal neuralgia. Other uses include treatment of neurogenic diabetes insipidus; certain psychiatric disorders, including schizoaffective illness, depression, agitation, behavioral disturbances related to dementia, resistant schizophrenia, and dyscontrol syndrome associated with limbic system dysfunction; alcohol withdrawal; fibromyalgia; neuropathy; status epilepticus; and refractory seizure disorders.

While the carbamazepine-cyclodextrin inclusion complexes of the present invention provide reduced toxicity and 100% bioavailability compared to other parenteral carbamazepine formulations such as a PEG400 formulation. Moreover, the complexes of the present invention are less nephrotoxic while providing similar solubilities and dissolution rates of carbamazepine-cyclodextrin complexes.

Further details of the preferred embodiments of the present invention are illustrated in the following examples, which are understood to be non-limiting.

EXAMPLES

Example 1

Preparation of Carbamazepine-Cyclodextrin Inclusion Complex

450 Grams of hydroxypropyl-beta-cyclodextrin (HPBCD) was dissolved in 2.0 L of deionized water to generate a 22.50 w/v solution. $^{13}C$, $^{15}N$-labeled carbamazepine (CBZ) [purchased from Cambridge Isotope Laboratories (CIL), 50 Frontage Road, Andover, Mass. 01810], 20 grams, was added to this solution. The resulting admixture was stirred for 24 hours at room temperature (20-25° C.). After 24 hours, the solution was sterile filtered through a sterile 0.22 micron Durapore filter into a sterile receiver. Previously sterilized ampoules were then filled and sealed under a nitrogen flush. The filled ampoules were stored at 2-8° C. The resulting inclusion complex had a CBZ concentration of approximately 10 mg/ml.

Example 2

Stability Testing

Ampoules containing 10.1 mg/ml carbamazepine-cyclodextrin inclusion complex were placed on room temperature stability studies and sampled every six months. CBZ was detected by HPLC using UV detection at 215 nm. Results are presented in Table 2.

TABLE 2

Stability of Intravenous, Stable-labeled Carbamazepine Solution

| Testing Date | Initial Concentration in Vial | % Recovery | Degradation Product-CBZ: iminostilbine |
|---|---|---|---|
| May 31, 2005 | 10.1 mg/ml | 104.65% | not detected |
| Nov. 10, 2004 | 10.1 mg/ml | 97.07% | not detected |
| May 2, 2004 | 10.1 mg/ml | 96.67% | not detected |

Example 3

Pharmacokinetics of Intravenous and Oral Carbamazepine in Patients on Maintenance Therapy Indwelling catheters were placed into the arms of test subjects. A single 100 mg dose of stable-labeled (non-radioactive) CBZ (SL-CBZ) was then infused over 10 minutes. At the end of the infusion, the subject's usual morning dose of oral CBZ, less 100 mg, was administered. Blood pressure, heart rate and rhythm, and infusion site discomfort were monitored during and for an hour after the infusion. A single blood sample was collected prior to the infusion and 12 samples were collected over the ensuing 96 hours. Plasma was separated from blood and analyzed, using a LC-MS assay, for CBZ and CBZ-epoxide, an active metabolite, and glucuronidated metabolite that is inactive. Unbound CBZ was measured following ultrafiltration. CBZ concentration-time data were analyzed using a non-compartmental approach with the pharmacokinetic software, WinNONLIN.

A validated LC-MS assay for SL-CBZ, CBZ and their respective epoxide metabolites was used. Carbamazepine-d${}_{10}$ (CBZ-d$_{10}$, C/D/N Isotopes, Quebec, Canada) was used as the internal standard. CBZ was assayed similar to that described by Osterloh and Bertilsson. (Oster-loh J, Bertilsson L. The absence of isotopic effect during the elimination of deuterium labeled carbamazepine in the rat. (Life Sci. 1978; 23:83-7.) To obtain a standard for CBZ-glucuronide, it was isolated from the urine of patients on CBZ monotherapy using a procedure similar to that previously published. (Sinz M W, Remmel R P. Analysis of lamotrigine and lamotrigine 2-N-glucuronide in guinea pig blood and urine by reserved-phase ion-pairing liquid chromatography. J Chromatogr 1991; 571:217-30) A 0.5 ml aliquot of patient plasma and 10 microliters of internal standard was added to blank plasma and extracted with 3 volumes of ethyl acetate. After shaking and centrifugation, the organic layer was removed and evaporated under nitrogen gas to dryness. Each sample was then redissolved with the addition of 25 microliters of ethyl acetate. Plasma samples were measured for unbound and total CBZ, CBZ glucuronide and CBZ-E by LCMS. Unbound drug was separated from the bound fraction by ultrafiltration. The mobile phase consists of 50% 0.05 M ammonium acetate buffer, pH 4.7, 50% MeOH at a flow rate of 0.4 ml/min, on a reverse phase C-18 column. For selected ion monitoring (SIM), signals at m/z 237 (CBZ), 239 ($^{13}C^{15}N_2$-CBZ), 253 (CBZ-epoxide), 255 $^{13}C^{15}N_2$-CBZ-epoxide) and 247 (CBZ-$d_{10}$) were measured with a PC-based Hewlett-Packard Chem-Station® software. The lower limit of detection is 0.05 micrograms/ml for CBZ. LC-MS method has been validated for the determination of [$^{13}C,^{15}N$]-carbamazepine, carbamazepine, and their 10,11-epoxide metabolites in human plasma. Over a concentration range of 1.5 to 12 micrograms/ml the percent coefficient of variance was ≤5%.

Table 3 provides the pharmacokinetic parameters for 76 subjects. The range of oral CBZ daily dose ranged from 100 mg to 2400 mg for subjects in this study. As can be seen, the absolute bioavailability of oral CBZ during maintenance therapy centers around 70-75% with 30 of the 56 subjects having bioavailabilities below 70%. The variability of bioavailability is also substantial with a range of 0.35 to 1.65. The highly variable bioavailability could be indicative of delayed release of drug from the various immediate and extended release oral formulations of CBZ or from continued absorption from an extended release dosage form into a subsequent dosing interval. The distribution volume at steady state (VSS) is 1.24±0.439 L/kg. This is a previously unknown value (due to the lack of an IV formulation) the now permits precise dosing of an IV formulation to attain a targeted plasma CBZ concentrations as might be required when initiating therapy in patients whose oral therapy has been interrupted for 12 or more hours.

Another clinically important observation is the prolonged CBZ elimination half-life under steady-state conditions. The mean value was determined to be 25.8 hours (range from 8.79 to 64.6 hours) in contrast with the reported range of 12 to 17 hours in the package insert for Tegretol® and Carbatrol®. The most likely explanation for this difference is the use of an SL-IV CBZ solution in the present study that permitted rigorous characterization of elimination for 2-3 half-lives while subjects continued to take their oral CBZ doses as prescribed. The extended half-lives observed in the adult subjects will limit the fluctuation of CBZ concentrations following IV administration every six hours, further reducing the risk of sub-therapeutic CBZ concentrations.

The present study utilized the 2-hydroxypropyl-β-cyclodextrin formulation for a drug solubilizing agent of SL-CBZ. The pharmacokinetic data obtained from this study, while not specifically designed to determine a full replacement IV dosing regimen, can assist in establishing the target dose for this study. The results from the present study demonstrate a wide range of CBZ bioavailability values among subjects, several of which had calculated bioavailability values greater than 100%. As a result, a bioavailability value of 70% has been chosen for use when dosing subjects in this sequential study. This value is similar to the median F value (67%) determined from subjects administered IV CBZ in the present study (n=76). The justification for using the median bioavailability value for correcting the dose for IV administration of CBZ in the current study assumes that the true bioavailability in subjects should not be greater than 100% especially at steady-state dosing levels. The value of 70% is between the calculated mean F value of 75% and the true rank order median value of 67%, and allows for an appropriate, calculable IV dose adjustment. The typical subject should then receive a daily IV dose that is 70% of that individual's daily oral dose. This can produce CBZ plasma concentrations from the IV dose that are comparable to those concentrations resulting from oral administration in the majority of subjects. Thus, the results of the present study provide initial safety and tolerability of a carbamazepine-cyclodextrin combination in subjects along with providing data that can be used to calculate the appropriate dose and dosing interval for replacement IV therapy.

Example 4

Preparation of CBZ Standard Solution Equipment

Shimadzu HPLC systems with autosampler, pumps, degassers, UV detector, column oven, system controllers, and Shimadzu Class VP system Software Cahn Microbalance
Shimadzu AY-120 Analytical balance pH meter, Orion pH/ISE Model #420 A LabnetVX 100 Vortex
Eppendorf Centrifuge 5415 D
Fisher Scientific FS30 Sonicator
LabQuake Shaker
Materials

| Material | Manufacturer | Lot No. |
|---|---|---|
| Carbamazepine | Spectrum | SA0491 |
| Carbamazepine | Orgamol | 899954 |

TABLE 3

Carbamazepine Summary Pharmacokinetics

|  | Age (yr) | Body Weight (kg) | F | T½ (hr) | AUCss (po) (μg-hr/mL) | AUC 0-∞ (μg-hr/mL) | VSS (L/kg) | CL (L/hr/kg) | CLSS/F (L/hr/kg) |
|---|---|---|---|---|---|---|---|---|---|
| N | 76 | 76 | 70 | 76 | 70 | 76 | 76 | 76 | 70 |
| Mean | 46.9 | 81.7 | 0.742 | 25.8 | 89.5 | 38.2 | 1.24 | 0.040 | 0.045 |
| (SD) | (15.7) | (17.7) | (0.29) | (11.2) | (29.3) | (15.3) | (0.439) | (0.015) | (0.024) |
| Min | 19.0 | 48.0 | 0.348 | 8.79 | 28.5 | 14.9 | 0.612 | 0.013 | 0.0087 |
| Median | 45.0 | 82.0 | 0.670 | 24.6 | 87.2 | 36.5 | 1.13 | 0.036 | 0.041 |
| Max | 87.0 | 151 | 1.65 | 64.6 | 168 | 94.5 | 3.17 | 0.089 | 0.122 |

Note:
The values of F, AUCss (po), and CLss/F included only 70 subjects due to 6 subjects only receiving the morning IV dose of CBZ. The range of oral CBZ daily dose ranged from 100 mg to 2400 mg.

-continued

| Material | Manufacturer | Lot No. |
|---|---|---|
| Cavitron 82004 | Cargill | H3M134P |
| Captisol | Cydex | CY03A020535 |
| Acetonitrile | Fisher | 031168 |
| Purified water | | |

Preparation of CBZ Standard Solution (0.05 mg/L)

Weigh out 5 mg of CBZ and place in a 100 ml volumetric flask. Fill to volume with 60% aqueous acetonitrile.

Preparation of Cyclodextrin Vehicles

The percent weight/volume cyclodextrin solutions were prepared by adding the appropriate amount of cyclodextrin to a flask and filling to the desired total volume (10 mL) with water, as shown in the following Table 4.

TABLE 4

| | Amount of Cyclodextrin (g) | | | | | | | | | | | | | |
|---|---|---|---|---|---|---|---|---|---|---|---|---|---|---|
| | 0.0 | 0.5 | 1.0 | 1.5 | 2.0 | 2.5 | 3.0 | 3.5 | 4.0 | 4.5 | 5.0 | 6.0 | 7.0 | 8.0 | 9.0 |
| Cyclodextrin in Water % (w/v) | 0 | 5 | 10 | 15 | 20 | 25 | 30 | 35 | 40 | 45 | 50 | 60 | 70 | 80 | 90 |

In initial assays, the flasks were graduated cylinders. In subsequent assays, the cyclodextrin was first dissolved in a small volume of water, quantitatively transferred to a volumetric flask which was then brought to volume with water.

Preparation of Samples for Phase Solubility

An excess of carbamazepine was added to each eppendorf tube. Appropriate vehicles were added to each tube and the final volumes were 1 mL.

Example 5

Phase Solubility

The solubility of CBZ was determined at ambient laboratory temperatures in various concentrations of aqueous Captisol and aqueous Cavitron (brand names of modified cyclodextrins useful in the present invention). The drug substance was added to a microcentrifuge tube and the appropriate vehicle was added. Periodically, the samples were centrifuged and then an aliquot was removed from the supernatant, diluted as necessary and assayed by HPLC to determine the concentration. The phase solubility was evaluated at least three times during each experiment to insure that the mixture achieved equilibrium. In general, the early concentration determination data (obtained approximately 2 hours after mixing the CBZ and the vehicle) were omitted because CBZ appeared to form supersaturated solutions initially before equilibration. The solubilities reported in Table 5 are the average of two or three concentration determinations obtained during the respective time course.

TABLE 5

Phase solubility data for CBZ in the presence of varying cyclodextrin concentrations

| | Cyclodextrin | | | | | | | | | | |
|---|---|---|---|---|---|---|---|---|---|---|---|
| | Captisol | | | | | | Cavitron | | | | | |
| | CBZ source | | | | | | | | | | | |
| Cyclodextrin conc (% w/v) | Spectrum | Orgamol Measured CBZ conc (mg/mL) | Orgamol | Ave | S.D. | % R.S.D. | Spectrum | Orgamol Measured CBZ conc (mg/mL) | Orgamol | Ave | S.D. | % R.S.D. |
| 0 | 0.2 | 0.2 | 0.2 | 0.2 | 0.0 | 0.0 | 0.3 | 0.2 | 0.2 | 0.2 | 0.0 | 13.3 |
| 5 | 2.4 | 2.2 | 2.4 | 2.3 | 0.1 | 4.9 | 3.8 | 2.7 | 3.0 | 3.2 | 0.6 | 18.0 |
| 10 | 6.2 | 4.1 | 4.6 | 5.0 | 1.1 | 22.1 | 4.1 | 5.4 | 5.6 | 5.0 | 0.8 | 16.2 |
| 15 | 6.9 | 6.4 | 7.7 | 7.0 | 0.7 | 9.4 | 12.3 | 8.2 | 8.4 | 9.6 | 2.3 | 24.0 |
| 20 | 9.4 | 9.2 | 10.3 | 9.6 | 0.6 | 6.1 | 16.4 | 10.9 | 11.1 | 12.8 | 3.1 | 24.4 |
| 25 | 11.8 | 11.4 | 12.3 | 11.8 | 0.5 | 3.8 | 14.8 | 14.0 | 14.3 | 14.4 | 0.4 | 2.8 |
| 30 | 14.6 | 13.5 | 15.2 | 14.4 | 0.9 | 6.0 | 17.9 | 15.9 | 16.2 | 16.7 | 1.1 | 6.5 |

TABLE 5-continued

Phase solubility data for CBZ in the presence of varying cyclodextrin concentrations

| | Cyclodextrin | | | | | | | | | | | |
|---|---|---|---|---|---|---|---|---|---|---|---|---|
| | Captisol | | | | | | Cavitron | | | | | |
| | | | | CBZ source | | | | | | | | |
| Cyclodextrin conc (% w/v) | Spectrum Measured CBZ conc (mg/mL) | Orgamol | Orgamol | Ave | S.D. | % R.S.D. | Spectrum Measured CBZ conc (mg/mL) | Orgamol | Orgamol | Ave | S.D. | % R.S.D. |
| 35 | 16.3 | 15.9 | 18.4 | 16.9 | 1.3 | 8.0 | 20.7 | 18.1 | 19.9 | 19.6 | 1.3 | 6.8 |
| 40 | 19.3 | 18.3 | 20.8 | 19.5 | 1.3 | 6.5 | 23.2 | 22.5 | 22.0 | 22.6 | 0.6 | 2.7 |
| 45 | 21.8 | 20.6 | 22.5 | 21.6 | 1.0 | 4.4 | 27.3 | 25.5 | 25.7 | 26.2 | 1.0 | 3.8 |
| 50 | 26.6 | 22.5 | 24.8 | 24.6 | 2.1 | 8.3 | 31.5 | 27.8 | 28.0 | 29.1 | 2.1 | 7.3 |

Figure 1B:
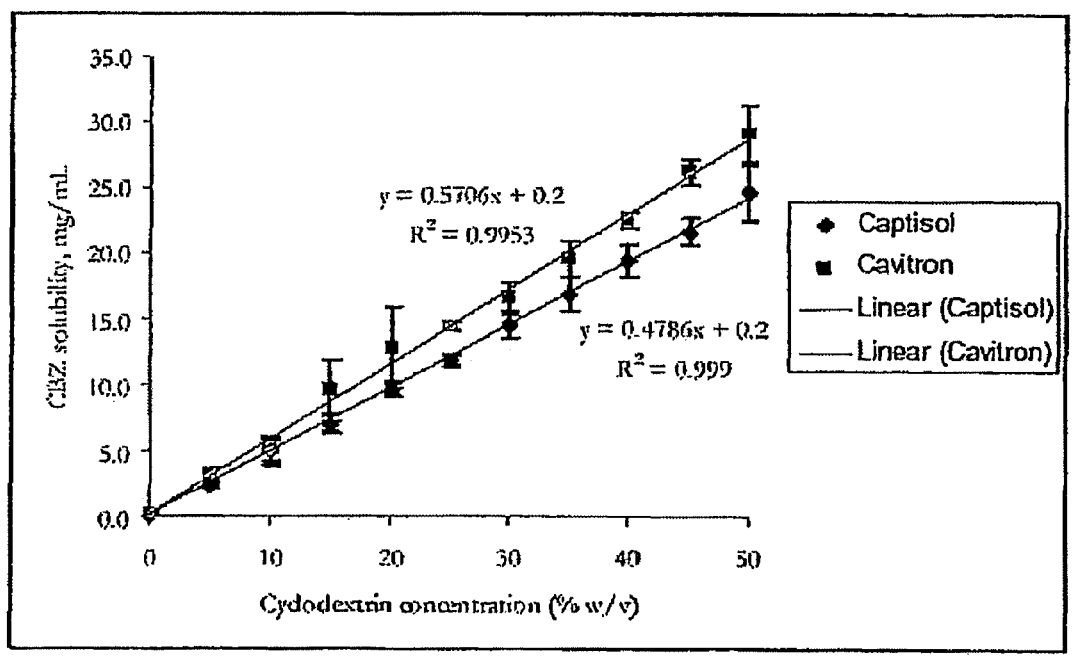
Figure 2:
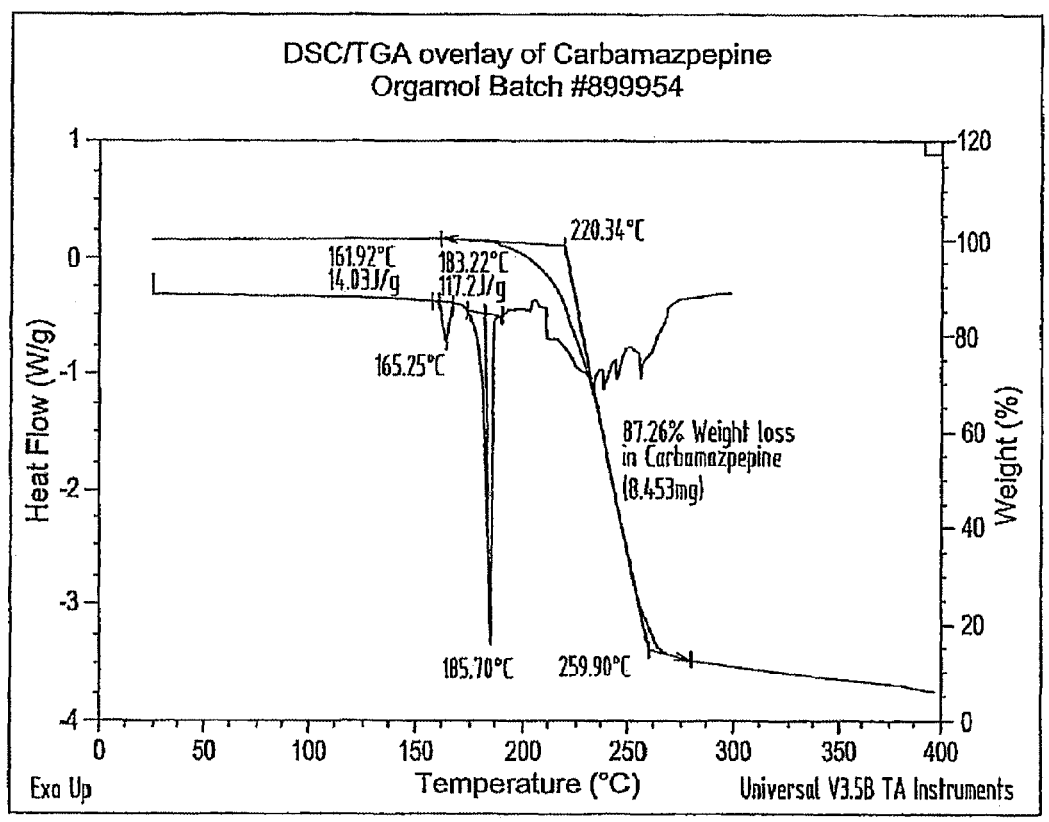
FIG. 2 shows the DSC/TGA overlay of Carbamazepine Orgamol batch #899954.
Figure 3:
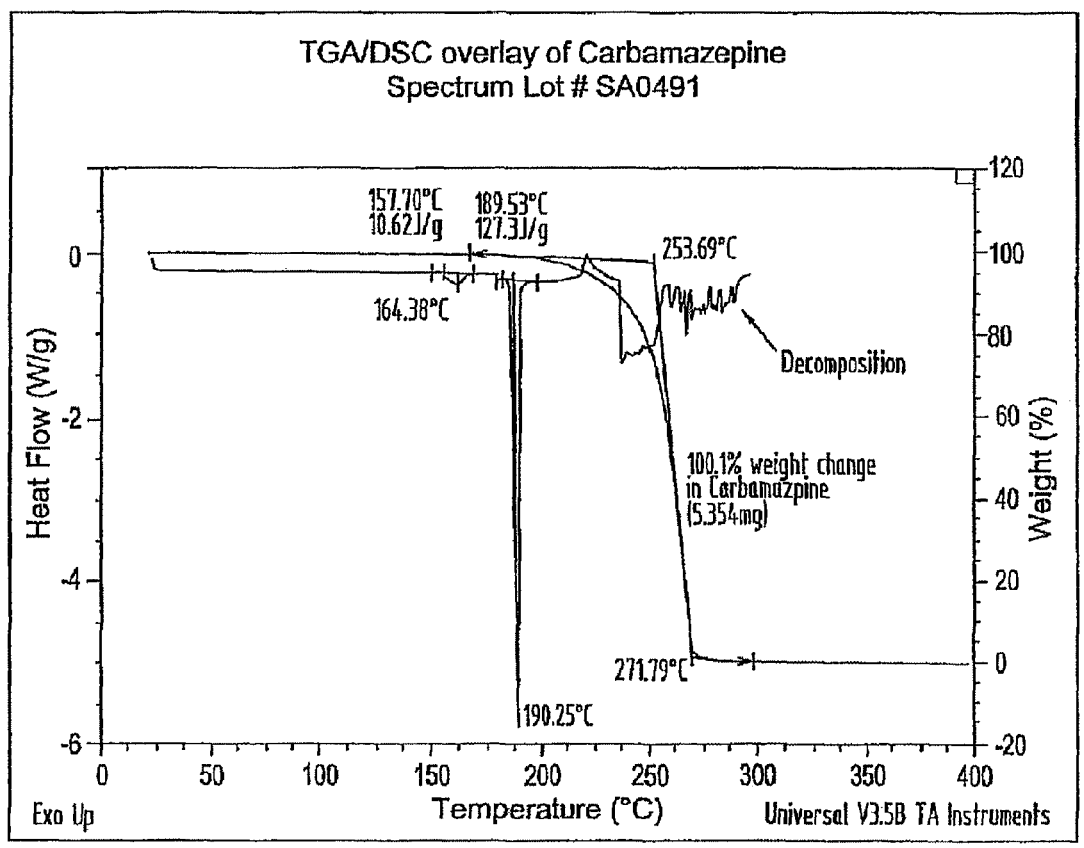
FIG. 3 shows the DSC/TGA overlay of Carbamazepine Spectrum batch #SA0491.

FIG. 1A shows a graphical representation of the compiled solubility data. From these data, it appears that the CBZ solubility at most cyclodextrin concentrations is marginally improved in Cavitron, as compared to Captisol. FIG. 1B shows the averaged solubility data with the associated standard deviations. The latter Figure also provides the trend lines for the averaged data.

Binding Constant

Assuming a 1:1 complex forms, the binding constant $K_{1:1}$ can be calculated, according to the relationship:

$$K_{1:1} = \text{slope}/[S_0(1-\text{slope})]$$

where S.sub.0 is the intrinsic solubility. The phase solubility data were expressed in terms of molarity and the equations of the lines were:

Captisol: $y = 0.4379x + 0.0008$ $r^2 = 0.9989$

Cavitron: $y = 0.3515x + 0.0008$ $r^2 = 0.9954$

From these equations, the binding constants of Captisol:CBZ and Cavitron:CBZ were found to be 974 and 677 $M^{-1}$, respectively. These relatively weak associations are within the range (100-20,000 $M^{-1}$) of those commonly seen with drug:cyclodextrin complexes (Crit. Rev. Ther. Drug Carrier Systems, 14 (1): 1-104, 1997). Stella et al. simulated drug release from cyclodextrins upon dilution (Advanced Drug Del. Rev. 36, 3-16, 1999) and suggested that if complexes are diluted 100-fold in the absence of any endogenous competing agent, approximately 30% of the drug will remain complexed, and if they are diluted 1000-fold, approximately 5% of the drug will remain complexed.

The minimal volume of distribution of a drug administered intravenously is based on the plasma volume, which is approximately 5% of the body weight. Therefore, in a 70 kg subject, the plasma volume is approximately 3.5 L. Alternatively, one could assume that the volume of distribution is extracellular water, accounting for approximately 30% of the total body weight, in which case the volume of distribution is about 21 L.

Table 6 shows the theoretical dilutions that would result from a 25 mg/mL formulation administered at different dose volumes. These calculations do not assume that any endogenous compounds might displace CBZ, and so they can be considered to be very conservative estimations. If a 20 mL dose were administered, the dilution ranges from 175-1,050-fold.

Based on the simulations of dilution effects, it appears that 70-95% of the CBZ will immediately dissociate from the inclusion complex in the blood if one assumes no interaction from endogenous agents.

TABLE 6

Theoretical extent of dilution for a 25 mg/mL CBZ formulation

| CBZ dose, mg | 200 | 500 | 800 |
|---|---|---|---|
| Total dose volume, mL | 8 | 20 | 32 |
| | Extent of Dilution | | |
| Plasma volume, 3,500 ml. | 438 | 175 | 109 |
| Extracellular volume, 21,000 mL | 2,625 | 1,050 | 656 |

Method of Vehicle Preparation

The phase solubility data from the first set of assays performed using the two cyclodextrins appear to be higher than all of the subsequent phase solubility experiments (data not shown). In this first assay, the cyclodextrin solutions were prepared by weighing the appropriate amount of cyclodextrin and adding it to a graduated cylinder and mixing to dissolve the solid. In all subsequent assays, the appropriate amount of cyclodextrin was added to a vial, dissolved, quantitatively transferred to a volumetric flask, filled to volume with water and mixed. This second method of vehicle preparation is more accurate and apparently significantly influenced the resulting phase solubility data. However, it is very difficult to prepare the cyclodextrin solutions volumetrically.

Effect of Cooling Saturated Solutions at 2-8° C.

The saturated CBZ/cyclodextrin solutions were placed in a 2-8° C. refrigerator and the appearances were recorded at various times. At 24 hours, all of the solutions showed a precipitate.

Example 6

Thermal Analysis

CBZ is known to exist in at least four different polymorphic states (J. Pharm. Sci. 90, 1106-1114, 1990). At one point in this study, it was suspected that the variability in the solubility data might be due to polymorphic differences. Thermal analyses using differential scanning calorimetry (DSC) and thermogravimetric analysis (TGA) were performed on the Spectrum CBZ and the Orgamol CBZ to determine if there were different polymorphs present in each product. Table 7 summarizes the experimental conditions and the thermal data.

TABLE 7

Thermal transitions obtained for CBZ from two manufacturers.

| Vendor Lot-Batch # | Thermogravimetric analysis Ramp 10° C./min from 25° C. to 400° C. | | Differential scanning calorimetry Ramp 5° C./min From 25° C. to 300° C. | | | | | | |
|---|---|---|---|---|---|---|---|---|---|
| | Initial weight (mg) | % weight loss | Sample weight (mg) | Onset peak 1 (° C.) | Peak 1 (° C.) | All Peak 1 (1/g) | Onset peak 2 (° C.) | Peak 2 (° C.) | AH Peak 2 (1/g) |
| Orgamol 899954 | 9.687 | 87.25 | 3.246 | 161.92 | 165.25 | 14.03 | 183.22 | 185.70 | 117.2 |
| Spectrum SA0491 | 5.351 | 100.1 | 4.510 | 157.7 | 164.38 | 10.62 | 189.53 | 190.25 | 127.3 |

Example 7

Appropriate Dosing Interval Determination

The most relevant factor in considering the dose adjustment for intravenously administered CBZ is for treatment centers to maintain plasma concentrations of CBZ above the therapeutic threshold. Following administration of 100 mg of IV CBZ, observed plasma concentrations followed a tri-exponential decay indicating a very fast distribution to tissues followed by a slower elimination of drug out of the body. Steady-state plasma concentrations of IV CBZ were predicted using the method of superposition. Plasma concentrations following a single dose of IV CBZ were scaled-up to steady-state conditions, assuming linear pharmacokinetics, using an accumulation ratio, a mean F of 0.7, and correcting for dose (see Equations 1 and 2). As a result, this calculation allows for a comparison of steady-state trough plasma concentrations following oral ($C_o$ and IV ($C_{6\ hr}$) administration of CBZ respectively assuming a dosing interval of once every six hours for the IV formulation.

the single IV dose; F is the absolute bioavailability; T is the dosing interval; and t is the time of each observed concentration.

The observed mean, oral steady-state trough ($C_o$) plasma concentration of CBZ following twice daily dosing was 8.98 (n/mL (n=62 evaluable subjects) (see Table 8, "Statistical Comparison of Trough Steady-State Carbamazepine Concentrations Following Oral BID Dosing or Q6 IV Dosing Based on Mean F=0.70"). The mean steady-state plasma concentration at the 6-hour time-point following IV administration of CBZ was predicted to be 8.04 (μg/mL. Statistical comparison of these two trough values following oral and IV administration of CBZ was found to be not statistically different (α=0.10; p=0.1931). Thus, the dosing frequency of every six hours following IV administration of CBZ outlined is appropriate to maintain plasma concentrations above this threshold and be comparable to trough levels following oral administration. Analysis of the same parameters at the 12-hour time-point, post-dose, indicated that the trough values were significantly different suggesting that an IV dosing regimen of every 12 hours would not be feasible to ensure the plasma concentration of CBZ does not fall below the therapeutic range.

TABLE 8

Statistical Comparison of Trough Steady-State Carbamazepine Concentrations Following Oral BID Dosing or Q6 IV Dosing Based on Mean F = 0.70

| Carbamazepine Concentration | N | Mean | Difference Between the Means | SE for the Difference in the Means | 90% CI for the Difference in the Means | p-value |
|---|---|---|---|---|---|---|
| $C_o$ (oral only) | 62 | 8.98 | 0.09456 | 0.7158 | (−0.254, 2.15) | 0.1931 |
| $C_{6\ hr}$ (IVonly)-Mean F | 62 | 8.04 | | | | |

$$F = \frac{AUC_{r,SS}(\text{Oral})}{AUC_{0-\infty}(IV)} \times \frac{\text{Dose}(IV)}{\text{Dose}(\text{Oral})} \quad \text{Equation 1}$$

$$C_{pSS}(IV) = C_{pSD}(t)(IV) + \frac{\text{Int} \exp^{-\lambda T} \exp^{-\lambda T}}{1 - \exp^{-\lambda T}} \cdot \frac{(D_{po}F)}{D_{IV}4} \quad \text{Equation 2}$$

Where $C_{pss}$(IV) is the plasma concentration (C) at steady state for IV administration; $C_{psD}$ is the plasma concentration after a single dose; Int is the y-intercept resulting from linear regression of the elimination phase; λ is the terminal elimination rate constant; $D_{po}$ is the total oral daily dose; $D_{IV}$ is

Example 8

Anticipated CBZ Maximum and Minimum Concentration Values During Intravenous Administration: Subjects at the Extreme of Carbamazepine Bioavailability A subset analysis of the subject data (n=47), including only those subjects taking extended release (ER) formulations of CBZ twice daily (as indicated by the product label), was performed to compare predicted maximum and minimum exposures of CBZ at steady-state administered via IV infusion to those observed following oral administration. CBZ concentration-time profiles following IV administration will differ from oral administration to the greatest extent for subjects on ER products, since these products provide formulation dependent control of the concentration-time profile. Subjects on extended release formulations experience the least fluctuation in concentrations and will maintain higher relative trough concentrations compared to any non-extended release product. Thus, the analysis in this subset gives a conservative assessment of potential differences in peak and trough exposures following IV administration.

This analysis included calculations of predicted $C_{max}$, $C_{min}$, and $AUC_{ss}$ values of CBZ for subjects predicted to be at steady-state on IV therapy. In order to predict steady-state plasma concentrations of IV CBZ, the same procedure for scaling plasma concentrations of CBZ as stated previously was implemented using Equations 1 and 2. Linear pharmacokinetics were assumed and plasma concentrations following a single 100 mg dose of IV CBZ were scaled-up to steady-state conditions using an accumulation ratio (determined using each individual's terminal elimination rate constant), and assuming a mean F of 0.7 for computation of the IV dose administered.

Following scale-up of the plasma concentrations of CBZ to steady-state, summary statistics of pharmacokinetic parameters were reported to compare the range of CBZ $C_{max}$, $C_{min}$, and AUC values between the oral (observed) and IV formulations of CBZ assuming a bioavailability (F) of 0.7 (See Table 9, "Summary Statistics of Predicted Steady-State Parameters Following Administration of IV or Oral Carbamazepine"). The steady-state PK parameters for the oral and IV formulations were obtained from data within the 12 hour dosing interval following administration of the ER products (Carbatrol® and Tegretol XR®) or the 6 hour interval after dosing of the IV product, respectively.

experience maximum plasma concentrations of CBZ that are in excess of the reported therapeutic range for this compound (see Table 9). Subjects taking high doses of oral CBZ compounded with an inherent low bioavailability could be at the greatest risk for adverse effects due to elevated CBZ plasma levels. The 70% dose adjustment would be the standard across all subjects administered replacement IV CBZ therapy to ensure the majority of subjects stay above the minimum (trough) therapeutic threshold and thus preventing seizures. If a subject's true bioavailability is less than the F value used for dosing, drug accumulation will occur when the inclusion complex is administered intravenously.

Example 9

Modeling and Simulation to Assess the Effect of Infusion Duration on $C_{max,ss}$ Following Administration of Intravenous Carbamazepine CBZ bioavailability is extremely variable among subjects and complicating factors such as formulations with different release rates, doses, and dosing intervals add to an already complex pharmacokinetic profile. Systemic exposures after IV administration of CBZ will not vary amongst subjects to the extent that systemic exposures vary after oral administration, since formulation characteristics and bioavailability are excluded as sources of variability following IV administration. Dose adjustments in subjects for IV CBZ replacement therapy must protect against low plasma concentration levels possibly leading to an increased risk in break through

TABLE 9

Summary Statistics of Predicted Steady-State Parameters Following Administration of IV or Oral Carbamazepine

| PK Parameter | N | Mean ± SD (µg/mL) | Minimum (µg/mL) | $5^{th}$ Percentile (µg/mL) | Median (µg/mL) | $95^{th}$ Percentile (µg/mL) | Maximum (µg/mL) |
|---|---|---|---|---|---|---|---|
| IV $C_{max}$SS (mean F = 0.7) | 47 | 11.75 ± 7.90 | 3.17 | 4.80 | 9.93 | 24.14 | 47.0 |
| IV $C_{min}$SS (mean F = 0.7) | 47 | 8.63 ± 6.85 | 1.65 | 2.48 | 6.50 | 18.64 | 41.04 |
| IV $AUC_{SS}$ (mean F = 0.7) | 47 | 121.83 ± 90.93 | 26.88 | 43.10 | 93.69 | 257.16 | 551.11 |
| Oral $C_{maxss}$* | 47 | 9.92 ± 2.99 | 2.89 | 4.98 | 9.81 | 14.60 | 17.10 |
| Oral $C_{minss}$* | 47 | 9.32 ± 2.93 | 2.89 | 4.32 | 9.44 | 14.55 | 16.69 |
| Oral $AUC_{ss}$ | 47 | 96.79 ± 28.08 | 28.48 | 50.11 | 96.01 | 145.51 | 167.58 |

*Oral Cmax, ss estimate is based on highest observed concentration, and may not be indicative of the subjects true Cmax, ss value due to sparse sampling; this study was not designed to assess the Cmax, ss of oral CBZ.
*Oral Cmax, ss estimate is based on highest observed concentration, and may not be indicative of the subjects true Cmax, ss value due to sparse sampling; this study was not designed to assess the Cmax, ss of oral CBZ.

The scaled-up steady-state CBZ concentrations were predicted based upon a 100 mg single IV dose infused over 10 minutes. The mean steady-state IV $C_{max}$ value was 11.75 (µg/mL, a plasma level that is higher compared to the mean oral $C_{max}$ at steady-state (see Table 9). Given the wide range of individual subject bioavailability values (F values) (see Table 3), subjects taking high doses of oral CBZ and subjects at the extreme lower end of bioavailability may seizures. Concurrently, the effects of increased transient CBZ exposures can occur in some subjects at the extreme low end of oral bioavailability or distribution volume.

The scaled IV CBZ concentration-time curves from the pharmacokinetic data of subjects dosed over 10 minutes reveal that the frequency distribution of $C_{max}$ values is unequal with a skewed tail at the extreme high end of $C_{max}$ values. At a mean bioavailability value for the population assigned to 70% (as is appropriate for the dosing in the present invention), the mean population $C_{max}$ value was 11.75 μg/mL with a median value of 9.93 μg/mL. The 95th percentile $C_{max}$ value was 24.14 μg/mL with a range of $C_{max}$ values from 3.17 μg/mL to 47.00 μg/mL (See Table 9, "Summary Statistics of Predicted Steady-State Parameters Following Administration of IV or Oral Carbamazepine").

Figure 4:
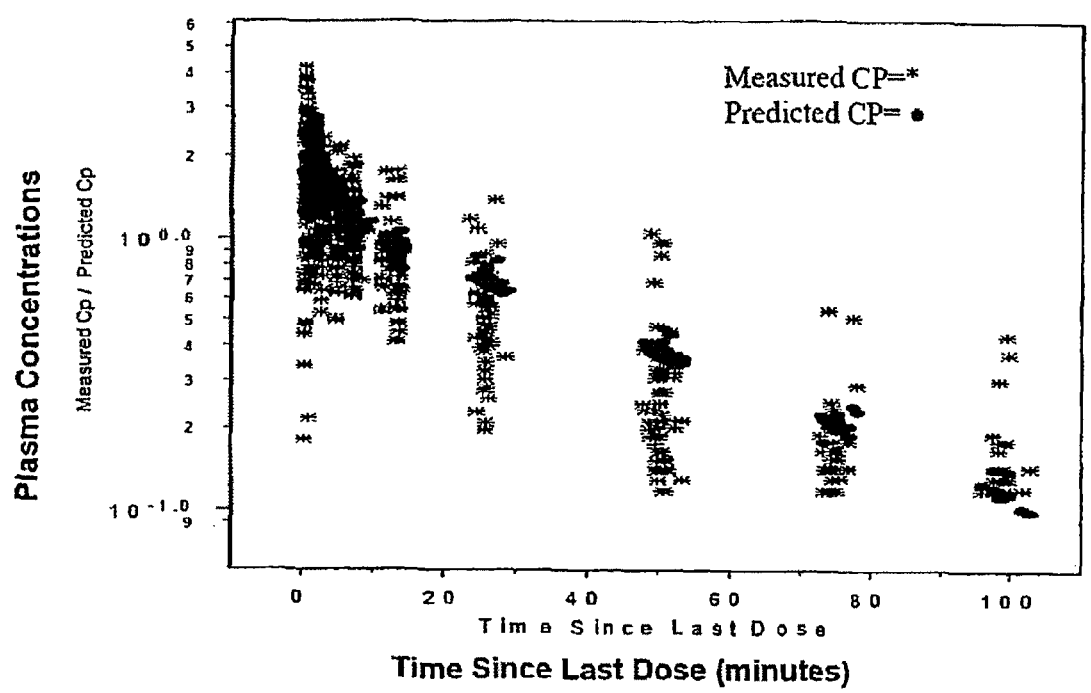
FIG. 4 shows the observed and predicted plasma concentration-time profiles following intravenous administration of 100 mg of carbamazepine using a 3-compartment PK model.
Figure 5:
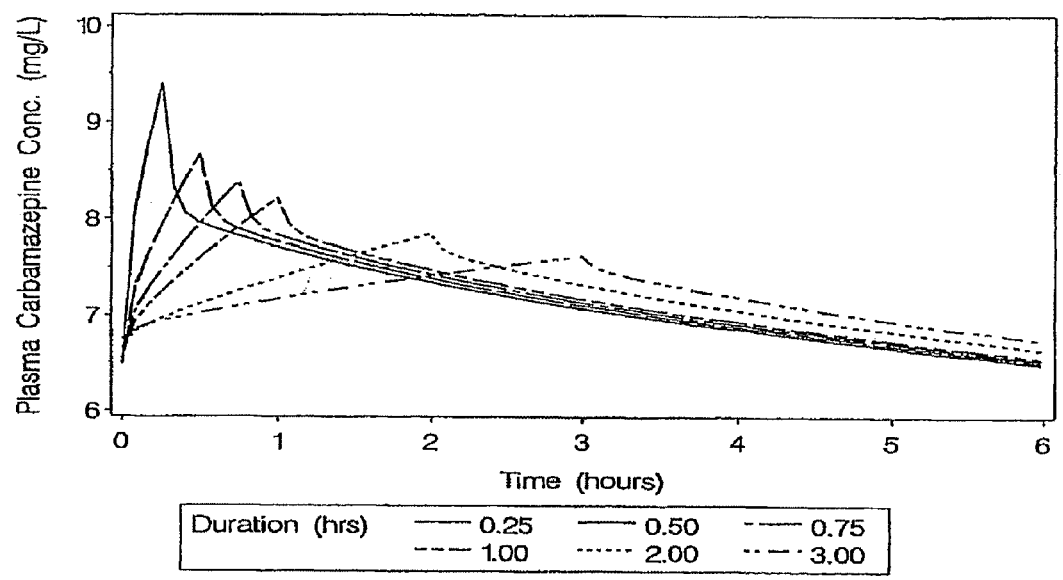
FIG. 5 shows the simulated plasma concentration-time profiles of carbamazepine following different infusion durations. The mean IV dose=150 mg, the average adjusted IV dose assuming F=0.7. Model parameters are the typical values parameters from the three-compartment model.

To assess the effect of infusion duration on $C_{max,ss}$ modeling and simulation was performed using the observed plasma concentrations of CBZ following IV administration of the single 100 mg dose. Based on various diagnostic plots assessing goodness-of-fit of the PK model, plasma concentrations of CBZ were best described by a three-compartment model, displaying a very rapid tissue distribution phase indicative of highly perfused tissues such as the liver, lung and brain, a second distribution phase indicative of deeper tissue penetration such as adipose tissue, and a more prolonged elimination phase (FIG. 4). The modeling results revealed that the mean t1/2 (α) and t1/2 (β) were rapid (approximately 2 minutes and approximately 65 minutes, respectively), indicating that elevated plasma levels of CBZ will be short-lived once an infusion is stopped. Population mean terminal t1/2 (γ) is approximately 28 hours, which is comparable to the value based on noncompartmental analysis (Table 3). Assuming that the pharmacokinetics are linear and stationary, using each subject's predicted parameters from the PK model, simulations were performed at steady-state to determine the effect of infusion duration on CBZ C.sub.max, ss (FIG. 5). The results showed a decrease in the mean $C_{max,ss}$ as the infusion duration increased (based upon a mean IV dose of 150 mg when dosed under steady state conditions). The mean, modeled $C_{max,ss}$ value after a 60 minute infusion was 10.68 μg/mL compared to 10.04 μg/mL after a 30 minute infusion compared to 11.69 μg/mL after a 15 minute infusion.

There was only an approximate 135 decrease in the mean $C_{max\,ss}$ value when the infusion duration was increased from 15 minutes to 1 hour.

Figure 6:
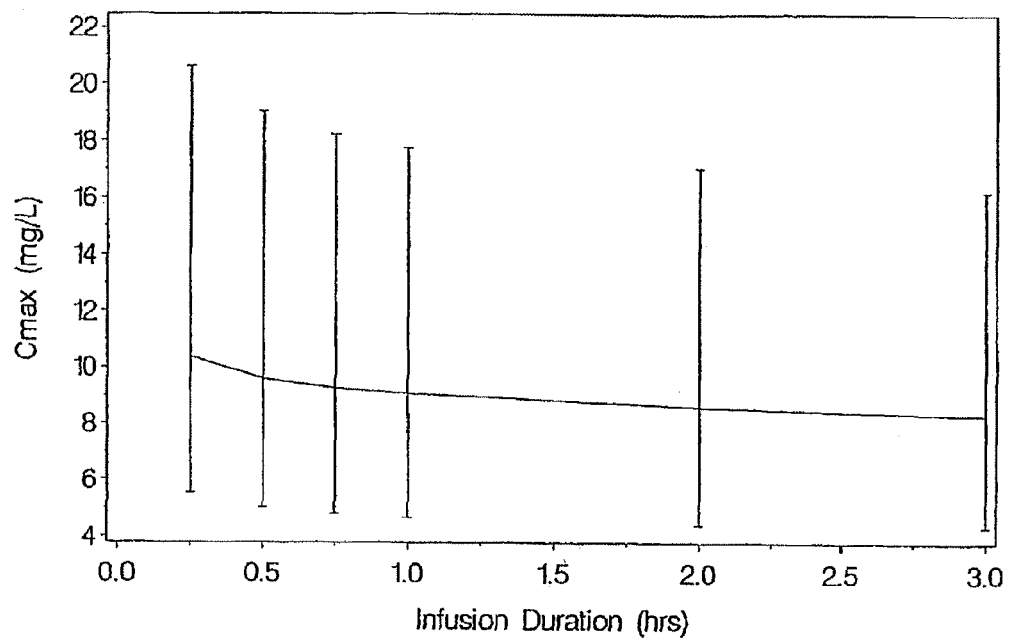
FIG. 6 shows the effect of infusion duration on Cmax,ss following IV administration of carbamazepine.

Notably, the peak concentration from the typical value simulation (150 mg IV dose) shown in FIG. 5 is comparable but differed slightly to that of the scaled, observed IV $C_{maxss}$ reported in Table 9 (approximately 9.50 μg/mL and 11.75 μg/mL respectively). The model dependent prediction (FIG. 6) more accurately captures the time point of the true maximum concentration, whereas the scaled, observed value (Table 9) is dependent upon the time of collection. The median (maximum) elapsed time between the end of infusion and the next time of collection was 5.3 (38.0) minutes. With t1/2 (α) of 2.2 minutes, considerable decay in concentration will occur during this time. For the full population, the actual median (maximum) time to observed $C_{max,ss}$ after the end of infusion was 5.8 (240) minutes. Additionally, all modeled infusions were precisely of 15 minutes duration. If actual infusion durations were greater than 15 minutes, $C_{max,ss}$ would be lower than predicted by the model. Finally, the typical value prediction modeled in FIG. 5 used each individual's set of model parameters and a typical dose (150 mg, the average adjusted IV dose assuming F=0.70), where the scaled observed values are based on the range of individual doses along with applying the superposition method at each observed concentration. As shown in FIG. 6, the average $C_{max,ss}$ values are similar with a 30 minute and 60 minute infusion.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

We claim:

1. An injectable pharmaceutical composition comprising
   i. about 10 mg/mL of carbamazepine,
   ii. about 25% weight/volume of a sulfoalkyl-cyclodextrin, and
   iii. a physiologically acceptable fluid,
   wherein said composition is administered parenterally, and
   wherein said composition contains carbamazepine in a dose of about 30% to about 100% of a human's oral maintenance dose.

2. The composition of claim 1, wherein the sulfoalkyl-cyclodextrin is sulfobutylether-7-β-cyclodextrin.

3. The composition of claim 1, wherein administration is intravenous, intraarterial, intramuscular, subcutaneous or intraperitoneal.

4. The composition of claim 1, wherein administration is intravenous.

5. The composition of claim 1, wherein said composition contains carbamazepine in a dose of about 65% to about 75% of the human's oral maintenance dose.

6. The composition of claim 1, wherein said composition provides an AUC for carbamazepine from about 70% to about 130% of the AUC for carbamazepine in the oral maintenance dose.

7. The composition of claim 1, wherein said composition provides a minimum plasma concentration of about 70% to about 130% of the minimum carbamazepine plasma concentration of the oral maintenance dose.

8. The composition of claim 1, wherein said composition provides a minimum plasma concentration of about 80% to about 125% of the minimum carbamazepine plasma concentration of the oral maintenance dose.

9. The composition of claim 1, wherein said composition provides trough carbamazepine concentrations within the therapeutic range.

10. The composition of claim 1, wherein said composition provides a carbamazepine half-life of about 8 to about 65 hours.

11. The composition of claim 1, wherein said composition provides a carbamazepine half-life of about 24 hours.

12. The composition of claim 1, wherein said composition has a dosing interval of every 6 hours.

13. An injectable pharmaceutical composition comprising
   i. about 10 mg/mL of carbamazepine,
   ii. about 25% weight/volume sulfobutylether-7-β-cyclodextrin, and
   iii. a physiologically acceptable fluid,
   wherein said composition is administered intravenously, and
   wherein said composition contains carbamazepine in a dose of about 30% to about 100% of a human's oral maintenance dose.

14. The composition of claim 13, wherein said composition contains carbamazepine in a dose of about 65% to about 75% of the human's oral maintenance dose.

15. The composition of claim 13, wherein said composition provides an AUC for carbamazepine from about 70% to about 130% of the AUC for carbamazepine in the oral maintenance dose.

16. The composition of claim 13, wherein said composition provides a minimum plasma concentration of about 70% to about 130% of the minimum carbamazepine plasma concentration of the oral maintenance dose.

17. The composition of claim 13, wherein said composition provides a minimum plasma concentration of about 80% to about 125% of the minimum carbamazepine plasma concentration of the oral maintenance dose.

18. The composition of claim 13, wherein said composition provides trough carbamazepine concentrations within the therapeutic range.

19. The composition of claim 13, wherein said composition provides a carbamazepine half-life of about 8 to about 65 hours.

20. The composition of claim 13, wherein said composition provides a carbamazepine half-life of about 24 hours.

21. The composition of claim 13, wherein said composition has a dosing interval of every 6 hours.

22. An injectable pharmaceutical composition comprising
   i. about 10 mg/mL of carbamazepine,
   ii. about 25% weight/volume sulfobutylether-7-β-cyclodextrin, and
   iii. a physiologically acceptable fluid,
   wherein said composition is administered intravenously,
   wherein said composition contains carbamazepine in a dose of about 65% to about 75% of a human's oral maintenance dose, and
   wherein said composition provides a minimum plasma concentration of about 70% to about 130% of the minimum carbamazepine plasma concentration of the oral maintenance dose.

23. The composition of claim 22, wherein said composition provides an AUC for carbamazepine from about 70% to about 130% of the AUC for carbamazepine in the oral maintenance dose.

24. The composition of claim 22, wherein said composition provides an AUC for carbamazepine from about 80% to about 125% of the AUC for carbamazepine in the oral maintenance dose.

25. The composition of claim 22, wherein said composition provides a minimum plasma concentration of about 80% to about 125% of the minimum carbamazepine plasma concentration of the oral maintenance dose.

26. The composition of claim 22, wherein said composition provides trough carbamazepine concentrations within the therapeutic range.

27. The composition of claim 22, wherein said composition provides a carbamazepine half-life of about 8 to about 65 hours.

28. The composition of claim 22, wherein said composition provides a carbamazepine half-life of about 24 hours.

29. The composition of claim 22, wherein said composition has a dosing interval of every 6 hours.

30. An injectable pharmaceutical composition comprising
   i. about 10 mg/mL of carbamazepine,
   ii. about 25% weight/volume sulfobutylether-7-β-cyclodextrin, and
   iii. a physiologically acceptable fluid,
   wherein said composition is administered intravenously,
   wherein said composition contains carbamazepine in a dose of about 65% to about 75% of a human's oral maintenance dose,
   wherein said composition provides a minimum plasma concentration of about 70% to about 130% of the minimum carbamazepine plasma concentration of the oral maintenance dose,
   wherein said composition provides an AUC for carbamazepine from about 70% to about 130% of the AUC for carbamazepine in the oral maintenance dose, and
   wherein said composition provides trough carbamazepine concentrations within the therapeutic range.

* * * * *

UNITED STATES PATENT AND TRADEMARK OFFICE
CERTIFICATE OF CORRECTION

PATENT NO. : 9,770,407 B2  
APPLICATION NO. : 14/051938  
DATED : September 26, 2017  
INVENTOR(S) : Cloyd et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 816 days.

Signed and Sealed this  
Fifteenth Day of September, 2020

Andrei Iancu  
*Director of the United States Patent and Trademark Office*